United States Patent [19]

Ishiguro et al.

[11] 4,302,463
[45] Nov. 24, 1981

[54] 1-AZAXANTHONE-3-CARBOXYLIC ACIDS AND THEIR PRODUCTION

[75] Inventors: Toshihiro Ishiguro; Kiyoshi Ukawa, both of Osaka; Akira Nohara, Kyoto, all of Japan

[73] Assignee: Takeda Chemical Industries, Ltd., Osaka, Japan

[21] Appl. No.: 185,954

[22] Filed: Sep. 10, 1980

[30] Foreign Application Priority Data

Oct. 2, 1979 [JP] Japan .................. 54/127694

[51] Int. Cl.$^3$ .................. A61K 31/44; C07D 49/52
[52] U.S. Cl. .................. 424/263; 546/89
[58] Field of Search .................. 546/89; 424/263

[56] References Cited

U.S. PATENT DOCUMENTS 4,143,042  3/1979  Nohara et al. .................. 546/89

OTHER PUBLICATIONS

Petersen; H. et al., "Herstellung and Reaktionen Von 2-Amino-4-oxo-4H-chromen-3-carbaldehyd", Liebigs Ann. Chem. 1976:1659.

Primary Examiner—John M. Ford
Assistant Examiner—Robert C. Whittenbaugh
Attorney, Agent, or Firm—Wegner & Bretschneider

[57] ABSTRACT

Novel 1-azaxanthone-3-carboxylic acid derivatives, which are shown by the following formula (I)

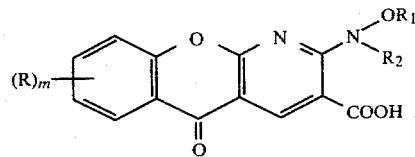

wherein R is hydrogen, alkyl, alkoxy or halogen; $R_1$ and $R_2$ are the same or different and each is hydrogen, alkyl or alkenyl; and m is 1 or 2; and their physiologically acceptable salts, are usable as effective medicines for preventing and/or treating allergic diseases. The compound of the formula (I) can be produced by reacting a compound of the formula:

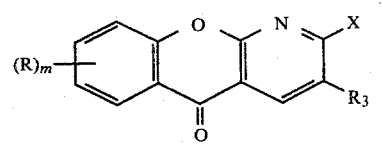

wherein R and m have the same meaning as defined above; $R_3$ is carboxyl or group which is convertible into carboxyl through hydrolysis; X is alkyl phosphate radical or halogen, with a compound of the formula:

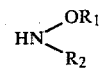

wherein $R_1$ and $R_2$ have the same meaning as defined above, or its salt, and conducting hydrolysis, if necessary.

22 Claims, No Drawings

1-AZAXANTHONE-3-CARBOXYLIC ACIDS AND THEIR PRODUCTION

The present invention provides a novel 1-azaxanthone-3-carboxylic acid derivatives of the formula (I):

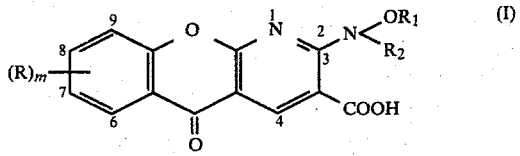

wherein R is hydrogen, alkyl, alkoxy or halogen; $R_1$ and $R_2$ are the same or different and each is hydrogen, alkyl or alkenyl; and m is 1 or 2; and their physiologically acceptable salts, which have excellent pharmacological activities such as antiallergic activity.

The object compound of the formula (I) can be produced by reacting a compound of the formula (II):

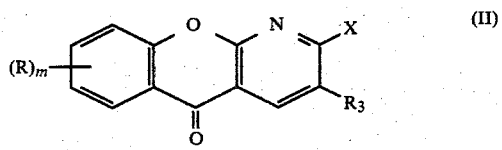

wherein R and m have the same meaning as defined above; $R_3$ is carboxyl or group which is convertible into carboxyl through hydrolysis; X is alkyl phosphate radical or halogen, with a compound of the formula (III)

wherein $R_1$ and $R_2$ have the same meaning as defined above, or its salt, and conducting hydrolysis, if necessary.

In the formulae (I) and (II), examples of the alkyl group represented by R may include straight-chain or branched-chain alkyl groups of 1 to 6 carbon atoms such as methyl, ethyl, propyl, isopropyl, butyl, isobutyl, t-butyl, pentyl and hexyl, and lower alkyl groups of 1 to 3 carbon atoms, among others, are practically preferred. As the halogen atom there may be mentioned chlorine, bromine, iodine and fluorine, and examples of the alkoxy group may include alkoxy groups having an alkyl moiety of 1 to 4 carbon atoms such as methoxy, ethoxy, propoxy and butoxy.

These substituents designated as R are the same or different, and one or two of these may substitute in arbitrary positions of the 6-, 7-, 8- and 9-positions of the azaxanthone ring.

As examples of the alkyl groups of the substituents, $R_1$ and $R_2$, there may be mentioned straight-chain or branched chain alkyl groups of 1 to 6 carbon atoms such as methyl, ethyl, propyl, isopropyl, butyl, isobutyl, t-butyl and hexyl, and examples of the alkenyl group may include alkenyl groups of 2 to 4 such as vinyl, propenyl, isopropenyl and butenyl. The halogen of the substituent, X, may be chlorine, bromine, iodine and fluorine, and as the alkyl moiety ($R_4$) of the alkyl phosphate radical

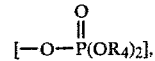

there may be mentioned alkyl groups of 1 to 3 carbon atoms such as methyl, ethyl and propyl. Examples of the group represented by $R_3$ which is convertible into carboxyl through hydrolysis may include nitrile, alkoxycarbonyl represented by the formula —$COOR_5$ (wherein $R_5$ is an alkyl group), and carbamoyl designated by the formula

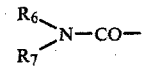

(wherein $R_6$ and $R_7$ are hydrogen or alkyl) which may be substituted, whereby the alkyl groups of $R_5$, $R_6$ and $R_7$ may be the same as those mentioned for the substituent group R, and lower alkyl groups of 1 to 3 carbon atoms, among others, are practically preferred.

The compound of the present invention as represented by the formula (I) is produced by substitution reaction of a compound of the formula (II) with a compound of the formula (III) or its salt (e.g., hydrochloride). Normally, the reaction is preferably carried out in an organic solvent, and as examples of such solvent there may be mentioned halogenated hydrocarbons such as chloroform, dichloromethane and 1,2-dichloroethane, hydrocarbons such as benzene, toluene and petroleum ether, ethers such as tetrahydrofuran, dioxane, ethyl ether, ethylene glycol dimethyl ether, etc., acetonitrile, dimethylformamide, formamide and dimethylsulfoxide.

Furthermore, the reaction is normally conducted in the presence of a base, and examples of such base may include tertiary amines such as triethylamine and tributylamine, heterocyclic bases such as pyridine and imidazole, and inorganic bases such as sodium hydrogencarbonate and sodium carbonate. These bases can be used in quantities ranging from catalytic amount to a large excess, and there is no particular limit to such quantities. Although no specific restriction is placed to reaction conditions such as reaction temperature and reaction time, the reaction is normally conducted in the temperature region of room temperature to 100° C. for a period of time within the range of several minutes to 24 hours.

Referring now to conditions of hydrolysis, the ordinary acidic or alkaline hydrolysis is employed. In the case of the acidic hydrolysis, sulfuric acid, hydrochloric acid, phosphoric acid, etc. are used, and the reaction is conducted by heating normally at a temperature in the vicinity of 50° to 150° C. in such acid alone or in conjunction with an organic solvent such as organic acids exemplified by formic acid and acetic acid. The reaction time varies with type of the compounds and is normally in the range of 1 hour to several days.

In the case of the alkaline hydrolysis, the reaction is conducted normally in the temperature range of 50° to 120° C., by use of sodium hydroxide, potassium hydroxide, barium hydroxide, calcium hydroxide, lithium hydroxide, tetramethylammonium hydroxide, etc. As the solvent for the hydrolysis reaction, which is not specifically restricted in choice unless it hinders the reaction, normally employed are methanol, ethanol, propanol, tetrahydrofuran, dioxane, etc.

The compound of the formula (I) can be converted to the corresponding organic amine salts, alkali metal salts or ammonium salts by reacting a compound (I) in the per se conventional manner with an organic amine (e.g. ethanolamine, diethanolamine, triethanolamine, dl-methylephedrine, 1-(3,5-dihydroxyphenyl)-L-isopropylaminoethanol, isoproterenol, dextromethorphan, hetrazan (diethylcarbamazine), diethylamine, triethylamine, etc.), an alkali metal hydroxide (e.g. sodium hydroxide, potassium hydroxide, etc.) or ammonia, for example by mixing them together and heating in a suitable solvent, e.g. water, methanol, ethanol, tetrahydrofuran, acetonitrile or the mixture of them.

The compounds of the formula (I) or salts thus produced exhibit the antiallergic activity, and are of value as the prophylactic anc therapeutic agents for allergic diseases such as allergic asthma, allergic dermatitis and hay fever.

In cases in which the compound of the formula (I) is for example used as the prophylactic and therapeutic agents for the above-mentioned allergic diseases, it is not only administered orally in an adult dose of, normally, about 1 to 500 mg/day in the forms of tablets, capsules, powders, solutions, etc., but also may be given in a suitable preparation form such as injections, spray inhalations, and ointments. These preparations can be formulated with a per se known carrier, vehicle, diluent or the like.

Furthermore, the starting compound of the formula (II) according to the present invention can be produced by the following procedure. That is to say, by the procedures disclosed in U.S. Pat. No. 4,143,042 or procedures similar thereto, the compound of the formula (IV):

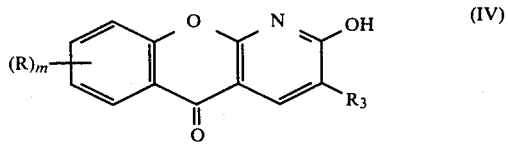

wherein R, $R_3$ and m have the same meaning as defined above; can be produced. By reacting the compound (IV) with phosphorus oxychloride in the presence or absence of phosphorus pentachloride, without any solvent or in a solvent such as chloroform, dichloroethane and benzene, normally at a temperature in the vicinity of 0° to 150° C. for several hours to 2 days, followed by treating with an alcohol such as methanol, ethanol or propanol, the compound of the formula (II) is produced. Further and if necessary, a compound of the formula (II) wherein $R_3$ is an alkoxycarbonyl group can be partially hydrolyzed by the above-mentioned alkaline hydrolysis to produce a compound of the formula (II) wherein $R_3$ is a carboxyl group.

The other starting compound of the formula (III) can be produced by the procedure disclosed in Chemical Abstract 68, 39053y (1968) [the original literature, Izv. Akad. Nauk. SSSR, Ser. Khim. 1967 (8), 1820] or procedures similar thereto.

Given below are the reference examples and examples to illustrate the present invention more specifically.

REFERENCE EXAMPLE 1

A suspension of 6.38 g of ethyl 2-amino-7-chloro-1-azaxanthone-3-carboxylate and 500 ml of acetic acid was heated to 80° C. To the suspension was dropwise added a solution of 6 g of NaNO₂ in 25 ml of water over 10 minutes and after heating at 80° C. for 30 minutes, added 20 ml of water, followed by heating at 80° C. for 4 hours. After allowing to stand the reaction solution at room temperature, the precipitated colorless needles were recovered by filtration, thus yielding 3.61 g of ethyl 7-chloro-2-hydroxy-1-azaxanthone-3-carboxylate. On the other hand, the mother liquor was concentrated to yield further crystals. Recrystallization from chloroform-ethanol yielded 2.25 g of colorless needles of the above compound. The total amount was 5.86 g. m.p. 237°–238° C.

REFERENCE EXAMPLE 2

A 2.0 g portion of 2-hydroxy-7-ethyl-1-azaxanthone-3-carboxylic acid was stirred together with 20 ml of phosphorus oxychloride and 1.5 g of phosphorus pentachloride at 100° C. for 1.5 hours. The phosphorus oxychloride was distilled off from the reaction mixture under reduced pressure and, to the residue under ice-cooling was dropwise added a saturated solution of sodium hydrogencarbonate to make alkaline. The mixture, after being made acid with 10% hydrochloric acid, was extracted with chloroform, followed by washing with water and drying over anhydrous sodium sulfate to distill off the solvent. The resulting residue was chromatographed on silica gel, and the fraction eluted with chloroform-acetone-formic acid (9:1:0.1) afforded crystals of 2-chloro-7-ethyl-1-azaxanthone-3-carboxylic acid. m.p., 233°–235° C.

By the same procedure, there were obtained the following compounds:

(1) 2-Chloro-7-methyl-1-azaxanthone-3-carboxylic acid, m.p., >300° C. (recrystallization solvent: chloroform-methanol).

(2) 2-Chloro-7-isopropyl-1-azaxanthone-3-carboxylic acid, m.p., 218°–220° C. (recrystallization solvent: chloroform-methanol).

REFERENCE EXAMPLE 3

A mixture of 2.6 g of ethyl 2-hydroxy-1-azaxanthone-3-carboxylate and 20 ml of phosphorus oxychloride was heated under reflux for 4 hours, and the phosphorus oxychloride was distilled off. Ethanol was added to the residual oily material and distilled off twice. Ethanol was added to the residue and, after cooling, the insolubles were recovered by filtration, thus yielding 4.2 g (wet weight) of a slightly yellowish solid. One g of the obtained solid was weighed out, dissolved in chloroform, chromatographed on a column of 50 g of silica gel, and eluted with chloroform-acetone-formic acid (20:1:0.1). The first fraction was concentrated, and recrystallized from ethanol, thus yielding 100 mg of colorless crystals of ethyl 2-chloro-1-azaxanthone-3-carboxylate. m.p., 155.5°–156.5° C.

From the second fraction, through recrystallization from ethanol in the same manner as described above, there was obtained 168 mg of colorless crystals of diethyl(3-ethoxy-carbonyl-1-azaxanthone-2)phosphate. m.p., 116°–117° C.

By the same procedure, there were produced the following compounds:

(1) Ethyl 2-chloro-7,9-dimethyl-1-azaxanthone-3-carboxylate, m.p., 164°–166° C. (recrystallization solvent: acetonitrile)

(2) Ethyl 2-chloro-9-methoxy-1-azaxanthone-3-carboxylate, m.p., 206°–207° C. (recrystallization solvent: ethanol)

(3) Ethyl 2-chloro-7-isopropyl-1-azaxanthone-3-carboxylate, m.p., 111°–112° C. (recrystallization solvent: isopropyl ether)

(4) Ethyl 2,7-dichloro-1-azaxanthone-3-carboxylate, m.p., 203°–204° C. (recrystallization solvent: chloroform-ethanol)

REFERENCE EXAMPLE 4

In 25 ml of chloroform was dissolved 1.65 g of ethyl 2-chloro-7-isopropyl-1-azaxanthone-3-carboxylate. To the solution were added 0.78 g of O-methylhydroxyamine hydrochloride and then, 1.88 g of triethylamine so as to allow them to react under reflux for 1.5 hours. After the conclusion of the reaction, 15 ml of water was added to the reaction solution for extraction. The chloroform layer was separated and dried over anhydrous sodium sulfate, followed by distilling off the solvent to yield the residue. The residue was recrystallized from chloroform-acetonitrile, thus affording ethyl 2-O-methylhydroxylamino-7-isopropyl-1-azaxanthone-3-carboxylate. m.p., 208°–209° C.

By the same procedure, there were obtained the following compounds:

(1) Ethyl 2-hydroxylamino-7-isopropyl-1-azaxanthone-3-carboxylate. Nuclear magnetic resonance spectrum (trifluoroacetic acid $d_1$ laveled) ppm: 1.43(6H,d,J=7 Hz), 1.49 (3H,t,J=7 Hz), 3.23(1H,quarter J=7 Hz), 4.70(2H,q,J=7 Hz), 7.80(1H,d,J=8 Hz), 8.10(1H,dd,$J_1$=2,$J_2$=8 Hz), 8.30(1H,d,J=2 Hz), 9.63(1H,s).

(2) Ethyl 2-O-ethylhydroxylamino-7-isopropyl-1-azaxanthone-3-carboxylate, m.p., 182°–184° C. (recrystallization solvent: acetonitrile)

(3) Ethyl 2-O-n-butylhydroxylamino-7-isopropyl-1-azaxanthone-3-carboxylate, m.p., 134°–135° C. (recrystallization solvent: acetonitrile)

(4) Ethyl 2-O-methylhydroxylamino-7,9-dimethyl-1-azaxanthone-3-carboxylate, m.p., 252°–254° C. (decomp.) (recrystallization solvent: acetonitrile-chloroform)

(5) Ethyl 2-O-allylhydroxylamino-7-ethyl-1-azaxanthone-3-carboxylate, m.p., 172°–174° C. (recrystallization solvent: acetonitrile)

(6) Ethyl 2-O-methylhydroxylamino-9-methoxy-1-azaxanthone-3-carboxylate, m.p., 254°–255° C. (decomp.) (recrystallization solvent: benzene)

(7) Ethyl 7-chloro-2-O-methylhydroxylamino-1-azaxanthone-3-carboxylate, m.p., 252°–253° C. (recrystallization solvent: chloroform-ethanol)

REFERENCE EXAMPLE 5

A 2.2 g portion of a mixture of ethyl 2-chloro-1-azaxanthone-3-carboxylate and diethyl (3-ethoxycarbonyl-1-azaxanthone-2)phosphate, as obtained in Reference Example 3, was added to 30 ml of chloroform, 660 mg of O-methylhydroxylamine hydrochloride and 2 ml of triethylamine, and, after heating under reflux for 16 hours, the mixture was washed with water and dried over anhydrous sodium sulfate. The chloroform was distilled off, and recrystallization of the residue from acetonitrile afforded crude crystals. The crystals were chromatographed on a column of 60 g of silica gel, and eluted with chloroform-acetone-formic acid (20:1:0.1). Recrystallization from ethanol yielded 900 mg of slightly yellowish crystals of ethyl 2-O-methylhydroxylamino-1-azaxanthone-3-carboxylate. m.p., 200.5°–201° C.

REFERENCE EXAMPLE 6

A 10.1 g portion of ethyl acetohydroxamate was added to a suspension of 4.8 g of sodium hydride in 41 ml of ether under stirring at 7° C. so as to conduct the reaction for 20 minutes. Then, 15 g of allyl bromide was added and stirred at room temperature for 2 hours.

Subsequently, the reaction solution was poured in water to extract with ether. The ether layer was separated and dried over anhydrous sodium sulfate, followed by distilling off the ether to obtain a oily material. The oily material was dissolved in 20 ml of ether, and 3 ml of concentrated hydrochloric acid was added and stirred at room temperature for 40 minutes. After cooling with ice, the precipitated crystals were recovered by filtration, thus yielding O-allylhydroxylamine hydrochloride. m.p., 176°–180° C. (decomp.).

REFERENCE EXAMPLE 7

In 333 ml of trifluoroacetic acid was dissolved 57.2 g of 2-amino-7-isopropyl-1-azaxanthone-3-carbonitrile, and to the solution was gradually added 17.1 g of NaNO$_2$ over 1.5 hours under ice-cooling and stirring. After stirring for further 30 minutes, the solution was poured in 3 l of ice-water. The resultant precipitates were collected by filtration, washed with water and suspended in 0.5 l of water, followed by addition of 1 l of 5% aqueous Na$_2$CO$_3$ solution and 33 g of triethanolamine, and further addition of 3.5 l of water and 1 l of ethyl acetate. After the mixture was well stirred and the insolubles were filtered off, the water layer was separated and extracted twice with each 1 l of ethyl acetate. After the insolubles were filtered off, the solution was made acid with 10% hydrochloric acid and allowed to stand at room temperature for 3 days. The resultant precipitates were recovered by filtration, washed with water, dried and recrystallized from dimethylformamide-ethanol.

By the above procedure there was yielded 47.1 g of colorless prisms of 2-hydroxy-7-isopropyl-1-azaxanthone-3-carbonitrile, m.p., >300° C.

REFERENCE EXAMPLE 8

To 41 g of 2-hydroxy-7-isopropyl-1-azaxanthone-3-carbonitrile were added 300 ml of phosphoryl chloride and 45 g of phosphorus pentachloride.

The mixture was stirred at 120° C. for 2 hours, followed by further addition of 5 g of phosphorus pentachloride, and further heated for 3 hours. The reaction mixture was cooled, and the resultant crystals were recovered by filtration, washed with isopropyl ether and dryed under reduced pressure.

By the above procedure there was produced 32.8 g of 2-chloro-7-isopropyl-1-azaxanthone-3-carbonitrile, m.p., 242°–243° C.

REFERENCE EXAMPLE 9

In 30 ml of chloroform was dissolved 0.6 g of 2-chloro-7-isopropyl-1-azaxanthone-3-carbonitrile and were further added 0.48 g of O-methylhydroxylamine hydrochloride and 0.6 g of triethylamine. The mixture was allowed to react under reflux for 2.5 hours. Then, 15 ml of water was added to the reaction mixture to wash.

The chloroform layer was separated, dried over anhydrous sodium sulfate, followed by distilling off the solvent. The residue was chromatographed on a column of 30 g of silica gel, and eluted with chloroform to give crystalline substance. Recrystallization from isopropyl ether-acetone yielded 0.360 g of 2-O-methylhydroxylamino-7-isopropyl-1-azaxanthone-3-carbonitrile, m.p., 196°–198° C.

REFERENCE EXAMPLE 10

To 0.10 g of 2-O-methylhydroxylamino-7-isopropyl-1-azaxanthone-3-carbonitrile was added 5 ml of polyphosphoric acid. The mixture was stirred at 110° C. for 2 hours and then, the reaction solution was poured into ice-water. The resultant precipitates were recovered by filtration, washed with water and dried. Recrystallization from ethanol yielded 65 mg of yellowish crystals of 2-O-methylhydroxylamino-7-isopropyl-1-azaxanthone-3-carboxamide, m.p., 257°–260° C. (decomp.).

EXAMPLE 1

A 1.4 g portion of ethyl 2-O-methylhydroxylamino-7-isopropyl-1-azaxanthone-3-carboxylate was stirred together with 3.5 ml of 50% sulfuric acid and 3.5 ml of acetic acid at 110° C. for 8 hours. The resultant solution was poured in warmed water, and the precipitated crystals were recovered by filtration, washed with water and dried. Recrystallization from acetic acid yielded 2-O-methylhydroxylamino-7-isopropyl-1-azaxanthone-3-carboxylic acid. m.p., 270°–274° C. (decomp.).

By the same procedure, there were obtained the following compounds.
 (1) 2-Hydroxylamino-7-isopropyl-1-azaxanthone-3-carboxylic acid, m.p., 237°–239° C. (recrystallization solvent: ethanol-water).
 (2) 2-O-ethylhydroxylamino-7-isopropyl-1-azaxanthone-3-carboxylic acid, m.p., 267°–271° C. (decomp.) (recrystallization solvent: acetic acid).
 (3) 2-O-n-butylhydroxylamino-7-isopropyl-1-azaxanthone-3-carboxylic acid, m.p., 244°–247° C. (decomp.) (recrystallization solvent: acetic acid).
 (4) 2-O-methylhydroxylamino-7,9-dimethyl-1-azaxanthone-3-carboxylic acid, m.p., 273°–277° C. (decomp.) (recrystallization solvent: acetic acid).

EXAMPLE 2

In 30 ml of chloroform was dissolved 62 mg of 2-chloro-7-isopropyl-1-azaxanthone-3-carboxylic acid, and to the solution were added 18 mg of O-methylhydroxylamine hydrochloride and then, 30 mg of triethylamine so as to allow them to react under reflux for 1.5 hours. Then, the solvent was distilled off, and 5 ml of 10% hydrochloric acid was added to the residue. The precipitated crystals were recovered by filtration, washed with water and dried. Recrystallization from acetic acid yielded 2-O-methylhydroxylamino-7-isopropyl-1-azaxanthone-3-carboxylic acid. m.p., 270°–274° C. (decomp.).

By the same procedure, there was produced 2-O-allylhydroxylamino-7-ethyl-1-azaxanthone-3-carboxylic acid. m.p., 261°–263° C. (decomp.) (recrystallization solvent: acetic acid).

EXAMPLE 3

To 10 ml of ethanol and 9 ml of 1.6% ethanolic KOH was added 500 mg of ethyl 2-O-methylhydroxylamino-1-azaxanthone-3-carboxylate, and the mixture was heated at 80° C. for 2 hours. Then, an additional 2 ml portion of ethanolic KOH was added, followed by heating at 80° C. for 2 hours. After the solvent was distilled off, 1 N hydrochloric acid was added to the residue to make acid, and the insolubles were recovered by filtration. The substances were heated with an excess of an aqueous triethanolamine solution, and the insoluble starting compound (ethyl 2-O-methylhydroxylamino-1-azaxanthone-3-carboxylate) was filtered out, followed by shaking the filtrate with ethyl acetate to extract the starting compound. The water layer separated was made acid with 1 N hydrochloric acid, and the resultant agar-like precipitate was heated to crystallize, followed by recovering by filtration 257 mg of crystals of 2-O-methylhydroxylamino-1-azaxanthone-3-carboxylic acid. To the starting compound recovered by filtration was added anew 10 ml of ethanol and 8 ml of 1.6% alcoholic KOH solution. After heating at 80° C. for 1 hour, the same treatment as described above yielded 124 mg of crystals of 2-O-methylhydroxylamino-1-azaxanthone-3-carboxylic acid. m.p., >300° C.

By the same procedure, there were produced the following compounds:
 (1) 2-O-allylhydroxylamino-7-ethyl-1-azaxanthone-3-carboxylic acid, m.p., 261°–263° C. (decomp.) (recrystallization solvent: acetic acid).
 (2) 2-O-methylhydroxylamino-9-methoxy-1-azaxanthone-3-carboxylic acid, m.p., 286°–288° C. (decomp.).

EXAMPLE 4

In 40 ml of chloroform was dissolved 5.9 g of ethyl 2-chloro-7-isopropyl-1-azaxanthone-3-carboxylate, and to the solution were added 1.2 g of N-methylhydroxylamine hydrochloride and 10 ml of triethylamine so as to allow them to react under reflux for 1 hour. Then, 15 ml of water and 15 ml of chloroform were added to the reaction solution to conduct extraction. The chloroform layer was separated and dried over anhydrous sodium sulfate, followed by distilling off the solvent to produce a dried residue. To the dried residue were added 40 ml of ethanol and then, 0.285 g of potassium hydroxide so as to allow them to react under stirring at 60° C. for 1.5 hours. Then, 15 ml of 10% hydrochloric acid was added to the reaction solution, and the precipitated crystals were recovered by filtration. Recrystallization from ethanol yielded 2-N-methylhydroxylamino-7-isopropyl-1-azaxanthone-3-carboxylic acid. m.p., 193°–195° C.

EXAMPLE 5

A mixture of 300 mg of ethyl 7-chloro-2-O-methylhydroxylamino-1-azaxanthone-3-carboxylate, 14 ml of ethanol and 6 ml of 1 N aqueous sodium hydroxide solution was heated at 100° C. for 2 hours and, after cooling, the resultant crystals were recovered by filtration and dissolved in about 10 ml of water under warming. The solution was made acid with 1 N hydrochloric acid and, then, warmed for 2 to 3 minutes. The precipitates were recovered by filtration, washed with water and dried. By the above procedure there was obtained 244 mg of 7-chloro-2-O-methylhydroxylamino-1-azaxanthone-3-carboxylic acid in a form of white solid, m.p., >300° C.

EXAMPLE 6

To 0.100 g of 2-O-methylhydroxylamino-7-isopropyl-1-azaxanthone-3-carbonitrile was added 4 ml of solution of 50% sulfuric acid-acetic acid (1:1) and the mixture was stirred at 120° C. for 12 hours. The reaction solution was poured into ice-water, and the resultant precipitates were recovered by filtration, washed with water and dried. Recrystallization from acetic acid yielded 69 mg of 2-O-methylhydroxylamino-7-isopropyl-1-azaxanthone-3-carboxylic acid, m.p., 270°–274° C. (decomp.).

By the same procedure, there was produced 2-O-methylhydroxylamino-7-isopropyl-1-azaxanthone-3-carboxylic acid from 2-O-methylhydroxylamino-7-isopropyl-1-azaxanthone-3-carboxamide.

EXAMPLE 7

In 4 ml of water was suspended 0.5 g of 2-O-methylhydroxylamino-7-isopropyl-1-azaxanthone-3-carboxylic acid, followed by addition of 1 ml of 1 N aqueous solution of sodium hydroxide. The solution was stirred at room temperature for a few minutes and, then, the insolubles were filtered off. The filtrate was concentrated to about half, to the concentrate was added 10 ml of tetrahydrofuran and the solution was cooled. The resultant yellowish crystals were recovered by filtration, washed with tetrahydrofuran and dried under reduced pressure.

By the above procedure, there was 0.16 g of yellowish prisms of sodium 2-O-methylhydroxylamino-7-isopropyl-1-azaxanthone-3-carboxylate, m.p., 233°–236° C. (decomp.).

EXAMPLE 8

To 0.33 g of 2-O-methylhydroxylamino-7-isopropyl-1-azaxanthone-3-carboxylic acid were added 4 ml of water and 0.20 g of triethanolamine. The mixture was stirred at room temperature for a few minutes and then, the insolubles were filtered off. The filtrate was concentrated to dryness and to the residue was added ethanol, followed by heating to dissolve. After cooling, the resultant precipitates were collected by filtration, washed with tetrahydrofuran and dried under reduced pressure.

By the above procedure, there was produced 0.22 g of pale yellowish needles of 2-O-methylhydroxylamino-7-isopropyl-1-azaxanthone-3-carboxylic acid triethanolamine salt, m.p. 149°–151° C.

EXAMPLE 9

An example of practical recipe in which the compound of this invention is utilized as remedies for an allergic disease is as follows:

| (Tablet) | | |
|---|---|---|
| (1) | 2-O-methylhydroxylamino-7-isopropyl-1-azaxanthone-3-carboxylic acid | 1 mg |
| (2) | lactose | 35 mg |
| (3) | corn starch | 169 mg |
| (4) | microcrystalline cellulose | 30 mg |
| (5) | magnesium stearate | 5 mg |
| | | 240 mg per tablet |

(1), (2), (3), $\frac{2}{3}$ quantity of (4) and half quantity of (5) are thoroughly mixed, and then the mixture is granulated. Remaining $\frac{1}{3}$ quantity of (4) and half of (5) are added to the granules and compressed into tablets. Thus prepared tablets can further be coated with a suitable coating agent, e.g. sugar.

What we claim is:

1. A compound of the formula:

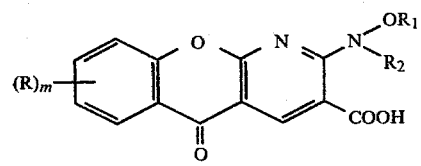

wherein R is hydrogen, alkyl, alkoxy or halogen; $R_1$ and $R_2$ are the same or different and each is hydrogen, alkyl or alkenyl; and m is 1 or 2, or its physiologically acceptable salt.

2. A compound as claimed in claim 1, wherein m is 1.
3. A compound as claimed in claim 1, wherein m is 2.
4. A compound as claimed in claim 1, wherein R is hydrogen.
5. A compound as claimed in claim 1, wherein R is alkyl of 1 to 6 carbon atoms.
6. A compound as claimed in claim 5, wherein R is alkyl of 1 to 3 carbon atoms.
7. A compound as claimed in claim 1, wherein R is alkoxy of 1 to 4 carbon atoms in the alkyl moieties.
8. A compound as claimed in claim 1, wherein R is halogen.
9. A compound as claimed in claim 1, wherein $R_1$ is alkyl of 1 to 6 carbon atoms and $R_2$ is hydrogen.
10. A compound as claimed in claim 1, wherein $R_1$ is alkenyl of 2 to 4 carbon atoms and $R_2$ is hydrogen.
11. A compound as claimed in claim 1, wherein $R_1$ is hydrogen and $R_2$ is alkyl of 1 to 6 carbon atoms.
12. A compound as claimed in claim 1, wherein the compound is 2-O-methylhydroxylamino-7-isopropyl-1-azaxanthone-3-carboxylic acid.
13. A compound as claimed in claim 1, wherein the compound is 2-O-ethylhydroxylamino-7-isopropyl-1-azaxanthone-3-carboxylic acid.
14. A compound as claimed in claim 1, wherein the compound is 2-O-n-butylhydroxylamino-7-isopropyl-1-azaxanthone-3-carboxylic acid.
15. A compound as claimed in claim 1, wherein the compound is 2-O-allylhydroxylamino-7-ethyl-1-azaxanthone-3-carboxylic acid.
16. A compound as claimed in claim 1, wherein the compound is 2-O-methylhydroxylamino-1-azaxanthone-3-carboxylic acid.
17. A compound as claimed in claim 1, wherein the compound is 2-O-methylhydroxylamino-9-methoxy-1-azaxanthone-3-carboxylic acid.
18. A compound as claimed in claim 1, wherein the compound is 2-hydroxylamino-7-isopropyl-1-azaxanthone-3-carboxylic acid.
19. A compound as claimed in claim 1, wherein the compound is 2-O-methylhydroxylamino-7,9-dimethyl-1-azaxanthone-3-carboxylic acid.
20. A compound as claimed in claim 1, wherein the compound is 2-N-methylhydroxylamino-7-isopropyl-1-azaxanthone-3-carboxylic acid.
21. A compound as claimed in claim 1, wherein the compound is 7-chloro-2-O-methylhydroxylamino-1-azaxanthone-3-carboxylic acid.
22. A composition for prophylaxis and therapy of allergic diseases which contains an anti-allergically effective amount of a compound of the formula:

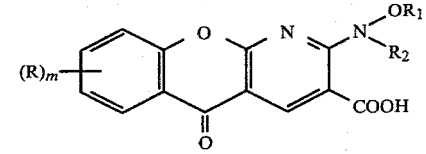

wherein R is hydrogen, alkyl, alkoxy or halogen; $R_1$ and $R_2$ are the same or different and each is hydrogen, alkyl or alkenyl; and m is 1 or 2, or its physiologically acceptable salt, and a pharmaceutically acceptable carrier, vehicle or diluent therefor.

* * * * *